United States Patent [19]

Downing et al.

[11] 4,299,618

[45] Nov. 10, 1981

[54] METHOD FOR INCREASING SOYBEAN YIELD

[75] Inventors: Charles R. Downing, Metuchen; Harold A. Kaufman, Piscataway, both of N.J.

[73] Assignee: Mobil Oil Corporation, New York, N.Y.

[21] Appl. No.: 785,612

[22] Filed: Apr. 7, 1977

Related U.S. Application Data

[63] Continuation-in-part of Ser. No. 588,276, Jun. 19, 1975, abandoned.

[51] Int. Cl.³ ............................................. A01N 33/04
[52] U.S. Cl. ......................................... 71/121; 71/76
[58] Field of Search .................................... 71/121, 76

[56] References Cited

U.S. PATENT DOCUMENTS 3,671,219  6/1972  Nickell .................................. 71/121

3,923,495  12/1975  Alt et al. ............................... 71/111

OTHER PUBLICATIONS

Shiralipour et al., Chem. Abst., vol. 73, (1970), 34044g.
Knight et al., Chem. Abst., vol. 71, (1969), 21086p.
Zenisceva et al., Chem. Abst., vol. 67, (1967), 20867z.
Plaut et al., Chem. Abst., vol. 63, (1965), 12243f.

*Primary Examiner*—Catherine L. Mills
*Attorney, Agent, or Firm*—Charles A. Huggett; Michael G. Gilman; Hastings S. Trigg

[57] ABSTRACT

Soybean crop yield can be increased by the foliar application of small amounts of trialkyl-2,4-dichlorobenzylammonium chlorides during certain stages of growth. Application to the Northern indeterminate varieties is at a rate of about 0.25–0.5 lb./acre during the 5–8 trifoliate leaf stage and application to the Southern determinate varieties is at a rate of about 0.5–0.75 lb./acre during the 10–11 trifoliate leaf stage.

4 Claims, No Drawings

METHOD FOR INCREASING SOYBEAN YIELD

CROSS-REFERENCE TO RELATED APPLICATIONS

This application is a continuation-in-part of copending application Ser. No. 588,276, filed June 19, 1975, now abandoned.

BACKGROUND OF THE INVENTION

1. Field of the Invention

This invention relates to a method of increasing soybean crop yield.

2. Description of the Prior Art

U.S. Pat. No. 3,218,356 discloses a trialiphatic compound such as tributyl-2,4-dichlorobenzylammonium chloride as a new composition of matter having utility as a fungicide.

U.S. Pat. No. 3,156,544 discloses a method of controlling relative stem growth of plants in general, consisting of treating plants with a compound of the formula:

$$R-N(CH_3)_3Y$$

wherein R is $C_2$–$C_3$ haloalkyl, alkylene, haloalkylene, cyanoalkyl, mercaptoalkyl, alkoxyalkyl and epithioalkyl and Y is a nonphytotoxic anion.

It is also known to regulate the growth of cereal such as wheat, barley or rye by use of a composition having as active ingredient, a combination of (2-chloroethyl)-trimethyl-ammonium chloride and, other agents such as alkali or ammonium salts of 2,3-dichloroisobutyric acid or N,N-diethylnicotinamide.

Plaut et al., in Israel J. Agric. Res. 14:4, pages 153-8 (1964), describe the effect of growth regulators on Brittle Wax beans under water distress, i.e., near-drought, conditions.

No reference has been found that is concerned with increasing soybean crop yield. Most significantly, no reference teaches the optimal times and rates of applying trialkyl 2,4-dichlorobenzylammonium chloride, dependent upon whether there is involved a Northern or a Southern variety of soybean.

SUMMARY OF THE INVENTION

This invention provides a method for increasing soybean crop yield that comprises applying to the foliage of soybean plants of small amounts of a trialkyl-2,4-dichlorobenzylammonium chloride; wherein, in the case of the Northern indeterminate varieties, application is at a rate of about 0.25–0.5 lb.a.i./acre during the fifth to eighth trifoliate leaf stage and, in the case of the Southern determinate varieties, application is at a rate of about 0.5–0.75 lb.a.i./acre during the tenth to eleventh trifoliate leaf stage.

DESCRIPTION OF SPECIFIC EMBODIMENTS

Accordingly, this invention is particularly directed to a method for increasing soybean crop yield, comprising contacting soybean plants with an effective amount of an alkyl-2,4-dichlorobenzylammonium chloride, or compositon thereof in sufficient amount to increase soybean yield. Foliar applications of the active compound are preferable. The amount of active compound applied will vary dependent upon whether a Northern variety or a Southern variety of soybean is involved, as is demonstrated hereinafter.

In general, the trialkyl compounds utilizable herein have between about 2 and 16 carbon atoms per alkyl group.

A non-limiting list of suitable compounds include:
N,N,N-tripropyl-2,4-dichlorobenzylammonium chloride
N,N,N-trioctyl-2,4-dichlorobenzylammonium chloride
N,N,N-tripentyl-2,4-dichlorobenzylammonium chloride
N,N,N-triisopentyl-2,4-dichlorobenzylammonium chloride
N,N,N-trihexyl-2,4-dichlorobenzylammonium chloride
N,N,N-triheptyl-2,4-dichlorobenzylammonium chloride
N,N,N-tridecyl-2,4-dichlorobenzylammonium chloride
N,N,N-tridodecyl-2,4-dichlorobenzylammonium chloride
N,N-dimethyl, N-octadecyl-2,4-dichlorobenzylammonium chloride
N,N-dimethylallyl-2,4-dichlorobenzylammonium chloride
N,N-dimethyl, N-decyl-2,4-dichlorobenzylammonium chloride The subject, 2,4-dichlorobenzylammonium chlorides embodied herein are readily available from a variety of commercial sources. However, they may also be prepared in accordance with the aforementioned U.S. Pat. No. 3,218,356. For example, 2,4-dichlorobenzyl chloride may be reacted over a period of several hours with excess tributylamine in an inert organic solvent at a temperature of from about 70°–85° C. The product (N,N,N-tributyl-2,4-dichlorobenzylammonium chloride) is then normally recovered at room temperature and is preferred.

The active ingredient (a.i.), i.e., the trialkyl ammonium chloride utilizable in this invention is most conveniently applied in conjunction with a liquid carrier containing a minor amount of said compound. Since the trialkyl ammonium chloride is water soluble, water will be the usual solvent. When water is used, it may contain a small quantity of any suitable surface active agent known to the art; many are commercially available. An example of a useful surface active agent is Tween-20; a mixture of 30% alkyl aryl sulfonates and 70% polyoxyethylene sorbitan esters or mixed fatty and resin acids.

In general, almost any inert liquid solvent or carrier material may be used as long as it is capable of dissolving or dispersing the active compound to substantial dilution and which is not harmful to the plant for its intended use. Especially advantageous are commonly used liquid carriers, for example, water, alcohol, ketones, amides, esters, mineral oils and vegetable oils.

In most instances, however, as noted previously an aqueous carrier is preferred. The carrier may also include a binding agent for holding the active compound in contact with the plant and/or various film-forming agents, as exemplified by mineral and ester waxes, and natural and synthetic resins and polymers to minimize the loss of the active compound from the treated plant by evaporation or the washing action of rain.

In carrying out the method of this invention, the treating agent may be applied in various ways. Preferably, the compositions are applied in the form of solutions or aqueous dispersions by spraying. In practice, compositions of the trialkyl-2,4-dichlorobenzylammonium chloride are applied as rather dilute solutions or dispersions of the active ingredient (a.i.) to all the leaves (i.e. foliar application) of the plant.

In practice, the rate of application is expressed in terms of pound of active ingredient per acre (hereinafter, lb.a.i./A). The rate used depends upon the variety of soybean, i.e., Northern or Southern, as does the growth stage of application for best results. For the Northern (indeterminate) varieties the rate of application is 0.25–0.5 lb.a.i./A at the fifth to eighth (5–8) trifoliate leaf stage. For the Southern (determinate) varieties the rate of application is 0.5–0.75 lb.a.i./A at the tenth to eleventh (10–11) trifoliate leaf stage.

EXAMPLE 1

Preparation Of Tributyl-2,4-Dichlorobenzyl Ammonium Chloride (A) Eighteen and fifty-four one-hundredths parts of tributylamine and 19.54 parts of 2,4-dichlorobenzyl chloride were placed in a 250 ml. glass stoppered flask. 70.8 parts of diethyl ether was added and the flask tightly stoppered and allowed to react at room temperature. After a considerable time an oil began to form and after 2 to 3 months, the product began to crystallize. At the end of six months, the crystals were filtered, washed with hexane and dried under vacuum. 16.7 parts of tributyl-2,4-dichlorobenzylammonium chloride was obtained, the compound having 3.33% nitrogen, the calculated value for nitrogen (for $C_{19}H_{32}Cl_3N$) is 3.69%.

(B) One hundred eighty-five and four-tenths parts of tributylamine and 97.8 parts of 2,4-dichlorobenzyl chloride were mixed with 78.5 parts of isopropanol and placed in a reactor equipped with a stirrer, condenser and thermometer. The mixture was heated for 6 hours with stirring at 80° C. after which the isopropanol and excess tributylamine were removed by distillation at 2 mm. and 80° C. 124.2 parts of crude product were obtained. The crude product was dissolved in 300 parts of water, and the water solution was washed with about 50 parts of hexane. The hexane was separated from the water and the water was removed by distillation, giving a recovery from the wash step of 67% tributyl-2,4-dichlorobenzylammonium chloride. Refractive index at 24° C., 1.529; Ionic Cl (Calc.) 9.31%; Cl (found) 9.34% (Volhard).

In copending application Ser. No. 588,276, data were presented based upon greenhouse tests. Yields were based upon green pod weight, application rates were not varied, and most applications were made at very early growth stages.

In order to obtain more meaningful data, field tests have been conducted. These tests were carried out in various parts of the United States and under varied climatic conditions. In many cases, application rates and times were varied in several field plots along with, in all cases, a check, i.e., an untreated plot.

Ideally, of course, a crop should be grown and harvested during a substantially normal growing season. By this is meant seasonable temperatures and normal or near normal rainfall for a given area.

In Table I, are presented soybean field test results for tests conducted in the United States during the 1976 growing season, together with pertinent data on soybean species, application rates, and trifoliate leaf stage of application. In all the Tables, "Rate Lb./A" is the amount of active ingredient applied per acre using conventional foliar spray application techniques. "Leaf stage" is the trifoliate leaf stage at which application is made. The cardinal numbers used are to be read as ordinal numbers. "Bu./A" is bushels per acre harvested, "Yield" indicating yield from treated plots and "Check" indicating yield from untreated plots.

In these tests, temperatures were generally seasonable, but rainfall varied. In the 1976 growing season, rainfall was about normal in Ohio and Texas and slightly below normal in Indiana. It was below normal in Iowa, Missouri, Nebraska, and New Jersey. In Mississippi there was near a drought condition which is reflected in low yield of soybean crop.

TABLE I

| State and Variety | Rate Lb./A | Leaf Stage | Bu./A Yield | % Increase |
|---|---|---|---|---|
| Indiana | | | | |
| Amsoy 71 | 0.25 | 3 | 42.8 | 13.8 |
| | 0.50 | 3 | 42.2 | 12.2 |
| | 0.75 | 3 | 42.5 | 13.0 |
| | 0.25 | 5 | 43.5 | 15.7 |
| | 0.50 | 5 | 38.8 | 3.2 |
| | 0.75 | 5 | 34.7 | −7.7 |
| | 0.25 | 7 | 41.1 | 9.3 |
| | 0.50 | 7 | 40.1 | 6.6 |
| | 0.75 | 7 | 31.5 | −16.2 |
| | Check | | 37.6 | |
| Iowa | | | | |
| Amsoy 71 | 0.5 | 3 | 37.4 | 8.7 |
| | 0.75 | 3 | 36.6 | 6.4 |
| | 1.0 | 3 | 39.5 | 14.8 |
| | 0.5 | 5–6 | 35.4 | 2.9 |
| | 0.75 | 5–6 | 36.9 | 7.3 |
| | 1.0 | 5–6 | 37.6 | 9.3 |
| | 0.5 | 7–8 | 35.1 | 2.0 |
| | 0.75 | 7–8 | 37.8 | 9.9 |
| | 1.0 | 7–8 | 39.5 | 14.8 |
| | Check | | 34.4 | |
| Corsoy | 0.5 | 3 | 37.2 | −1.6 |
| | 0.75 | 3 | 34.8 | −7.9 |
| | 1.0 | 3 | 37.1 | −1.9 |
| | 0.5 | 5–6 | 38.4 | 1.6 |
| | 0.75 | 5–6 | 35.4 | −6.3 |
| | 1.0 | 5–6 | 36.6 | −3.2 |
| | 0.5 | 7–8 | 39.6 | 4.8 |
| | 0.75 | 7–8 | 40.8 | 7.9 |
| | 1.0 | 7–8 | 35.9 | −5.0 |
| | Check | | 37.8 | |
| Beason | 0.5 | 3 | 35.5 | −16.1 |
| | 0.75 | 3 | 40.8 | −3.5 |
| | 1.0 | 3 | 34.6 | −18.2 |
| | 0.5 | 5–6 | 37.3 | −11.8 |
| | 0.75 | 5–6 | 34.1 | −19.4 |
| | 1.0 | 5–6 | 39.2 | −7.3 |
| | 0.5 | 7–8 | 35.8 | −15.4 |
| | 0.75 | 7–8 | 38.5 | −9.0 |
| | 1.0 | 7–8 | 38.0 | −10.2 |
| | Check | | 42.3 | |
| Hark | 0.5 | 3 | 39.0 | −9.1 |
| | 0.75 | 3 | 35.8 | −16.6 |
| | 1.0 | 3 | 37.6 | −12.4 |
| | 0.5 | 5–6 | 37.4 | −12.8 |
| | 0.75 | 5–6 | 39.9 | −7.0 |
| | 1.0 | 5–6 | 38.0 | −11.4 |
| | 0.5 | 7–8 | 40.3 | −6.1 |
| | 0.75 | 7–8 | 37.7 | −12.1 |
| | 1.0 | 7–8 | 38.6 | −10.0 |
| | Check | | 42.9 | |
| Wayne | 0.5 | 3 | 36.0 | −5.3 |
| | 0.75 | 3 | 36.0 | −5.3 |
| | 1.0 | 3 | 40.7 | 6.3 |
| | 0.5 | 5–6 | 34.4 | −9.5 |
| | 0.75 | 5–6 | 39.2 | 3.2 |
| | 1.0 | 5–6 | 35.9 | −5.5 |
| | 0.5 | 7–8 | 42.5 | 11.8 |
| | 0.75 | 7–8 | 38.6 | 1.6 |
| | 1.0 | 7–8 | 34.6 | −8.9 |
| | Check | | 38.0 | |
| Wells | 0.5 | 3 | 40.5 | 3.8 |
| | 0.75 | 3 | 39.4 | 1.0 |
| | 1.0 | 3 | 38.7 | −0.8 |
| | 0.5 | 5–6 | 42.4 | 8.7 |
| | 0.75 | 5–6 | 38.0 | −2.6 |
| | 1.0 | 5–6 | 40.9 | 4.9 |

TABLE I-continued

| State and Variety | Rate Lb./A | Leaf Stage | Bu./A Yield | % Increase |
|---|---|---|---|---|
| | 0.5 | 7-8 | 41.7 | 6.9 |
| | 0.75 | 7-8 | 40.8 | 4.6 |
| | 1.0 | 7-8 | 41.6 | 6.7 |
| | Check | | 39.0 | |
| Williams | 0.5 | 3 | 35.7 | 6.3 |
| | 0.75 | 3 | 38.4 | 14.3 |
| | 1.0 | 3 | 34.0 | 1.2 |
| | 0.5 | 5-6 | 38.9 | 15.8 |
| | 0.75 | 5-6 | 34.3 | 2.1 |
| | 1.0 | 5-6 | 35.6 | 6.0 |
| | 0.5 | 7-8 | 40.7 | 21.1 |
| | 0.75 | 7-8 | 34.1 | 1.5 |
| | 1.0 | 7-8 | 34.6 | 3.0 |
| | Check | | 33.6 | |
| Mississippi Lee 68 | 0.25 | 4-7 | 15.8 | 13.7 |
| | 0.5 | 4-7 | 17.0 | 22.3 |
| | 0.75 | 4-7 | 10.2 | −26.6 |
| | 0.25 | 10-11 | 9.6 | −30.9 |
| | 0.5 | 10-11 | 16.3 | 17.3 |
| | 0.75 | 10-11 | 8.9 | −35.0 |
| | Check | | 13.9 | |
| Missouri Mitchell | 0.25 | 5 | 43.9 | 2.6 |
| | 0.5 | 5 | 40.8 | −4.7 |
| | 0.75 | 5 | 44.4 | 3.7 |
| | 0.25 | 7 | 43.8 | 2.3 |
| | 0.5 | 7 | 42.1 | −1.6 |
| | 0.75 | 7 | 41.6 | −2.8 |
| | Check | | 42.8 | |
| SRF 425 | 0.25 | 5 | 39.8 | 1.0 |
| | 0.5 | 5 | 38.3 | −2.8 |
| | 0.75 | 5 | 42.6 | 8.1 |
| | 0.25 | 7 | 38.7 | −1.8 |
| | 0.5 | 7 | 37.6 | −4.6 |
| | 0.75 | 7 | 39.3 | −0.3 |
| | Check | | 39.4 | |
| Williams | 0.25 | 5 | 46.6 | 1.1 |
| | 0.5 | 5 | 45.9 | −0.4 |
| | 0.75 | 5 | 46.7 | 1.3 |
| | 0.25 | 7 | 47.7 | 3.5 |
| | 0.5 | 7 | 44.9 | −2.6 |
| | 0.75 | 7 | 46.8 | 1.5 |
| | Check | | 46.1 | |
| Nebraska Amsoy 71 | 0.25 | 3 | 22.9 | −12.9 |
| | 0.5 | 3 | 24.7 | −6.1 |
| | 0.25 | 5 | 26.3 | 0.0 |
| | 0.5 | 5 | 26.4 | 0.4 |
| | 0.25 | 7 | 25.9 | −1.5 |
| | 0.5 | 7 | 25.0 | −4.9 |
| | Check | | 26.3 | |
| New Jersey Kent | 0.25 | 7-8 | 22.9 | −6.9 |
| | 0.5 | 7-8 | 26.4 | 7.3 |
| | 1.0 | 7-8 | 27.8 | 13.0 |
| | Check | | 24.6 | |
| Ohio Beeson | 0.5 | 8 | 27.4 | 29.2 |
| | Check | | 21.2 | |
| Texas Bragg | 0.5 | 7 | 34 | −12.8 |
| | 0.75 | 7 | 38 | −2.6 |
| | 0.5 | 10-11 | 35 | −10.2 |
| | 0.75 | 10-11 | 40 | 2.6 |
| | Check | | 39 | |

Tables II and III are based upon the data in Table I. They set forth what appears to be the optimum rate and time of each area and varieties tested. Table II presents data for the Northern indeterminate soybean varieties and Table III presents data for the Southern determinate soybean varieties

TABLE II

| State and Variety | Rate Lb./A | Leaf Stage | Bu./A Yield | Check | % Increase |
|---|---|---|---|---|---|
| Indiana Amsoy 71 | 0.25 | 5 | 43.5 | 37.6 | 15.7 |
| Iowa Amsoy 71 | 1.0 | 3 | 39.5 | 34.4 | 14.8 |
| Amsoy 71 | 1.0 | 7-8 | 39.5 | 34.4 | 14.8 |
| Cosoy | 0.75 | 7-8 | 40.8 | 37.8 | 7.9 |
| Wayne | 0.5 | 7-8 | 42.5 | 38.0 | 11.8 |
| Wells | 0.5 | 5-6 | 42.4 | 39.0 | 8.7 |
| Williams | 0.5 | 7-8 | 40.7 | 33.6 | 21.1 |
| Missouri Michell | 0.75 | 5 | 44.4 | 42.8 | 3.7 |
| SRF 425 | 0.75 | 5 | 42.6 | 39.4 | 8.1 |
| Williams | 0.25 | 7 | 47.7 | 46.1 | 3.5 |
| Nebraska Amsoy 71 | 0.5 | 5 | 26.4 | 26.3 | 0.4 |
| New Jersey Kent | 1.0 | 7-8 | 27.8 | 24.6 | 13.0 |
| Ohio Beason | 0.5 | 8 | 27.4 | 21.2 | 29.2 |

TABLE III

| State and Variety | Rate Lb./A | Leaf Stage | Bu./A Yield | Check | % Increase |
|---|---|---|---|---|---|
| Mississippi Lee 68 | 0.5 | 4-7 | 17.0 | 13.9 | 22.3 |
| Texas Bragg | 0.75 | 10-11 | 40 | 39 | 2.6 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for increasing soybean crop yield that comprises applying to the foliage of soybean plants of small amounts of a trialkyl-2,4-dichlorobenzylammonium chloride having 2-16 carbon atoms per alkyl group; wherein, in the case of the Northern indeterminate varieties, application is at a rate of about 0.25-0.5 lb.a.i./acre during the fifth to eighth trifoliate leaf stage and, in the case of the Southern determinate varieties, application is at a rate of about 0.5-0.75 lb.a.i./acre during the tenth to eleventh trifoliate leaf stage.

2. The method of claim 1 wherein the trialkyl ammonium chloride is tributyl-2,4-dichlorobenzylammonium chloride.

3. The method of claim 2 wherein application is to a Northern indeterminate variety of soybean at a rate of about 0.25-0.5 lb.a.i./acre during the fifth to the eighth trifoliate leaf stage.

4. The method of claim 2, wherein application is to a Southern determinate variety of soybean at a rate of about 0.5-0.75 lb.a.i./acre during the tenth to eleventh trifoliate leaf stage.

* * * * *